United States Patent [19]

Moeller et al.

[11] Patent Number: 4,833,147

[45] Date of Patent: May 23, 1989

[54] SEBOSUPPRESSIVE COMPOSITIONS AND METHOD FOR SUPPRESSING SEBACEOUS GLAND ACTIVITY

[75] Inventors: Hinrich Moeller; Siegfried Wallat, both of Monheim, Fed. Rep. of Germany

[73] Assignee: Henkel Kommanditgesellschaft auf Aktien, Duesseldorf, Fed. Rep. of Germany

[21] Appl. No.: 23,056

[22] Filed: Mar. 6, 1987

[30] Foreign Application Priority Data

Mar. 17, 1986 [DE] Fed. Rep. of Germany ....... 3608852

[51] Int. Cl.$^4$ .......................... A61K 7/06; A61K 7/08; A61K 31/095
[52] U.S. Cl. .............................. 514/264; 424/DIG. 4; 424/70; 514/568; 514/864
[58] Field of Search ........................ 514/264, 864, 568

[56] References Cited

U.S. PATENT DOCUMENTS

| | | | |
|---|---|---|---|
| 3,957,994 | 5/1976 | Schroer ................................ | 514/264 |
| 4,107,306 | 8/1978 | Voorhees ............................. | 514/264 |
| 4,141,976 | 2/1979 | Voorhees ............................. | 424/240 |
| 4,390,532 | 6/1983 | Stuttgen et al. ..................... | 514/264 |
| 4,493,823 | 1/1985 | Moller et al. ........................ | 514/864 |
| 4,503,244 | 3/1985 | Möller et al. ........................ | 514/544 |
| 4,613,622 | 9/1986 | Moeller et al. ...................... | 514/864 |
| 4,668,705 | 5/1987 | Moeller et al. ...................... | 514/864 |
| 4,683,244 | 7/1987 | Moeller et al. ...................... | 514/568 |

FOREIGN PATENT DOCUMENTS

| | | | |
|---|---|---|---|
| 54174 | 6/1982 | European Pat. Off. ............ | 514/864 |
| 2559384 | 7/1977 | Fed. Rep. of Germany ...... | 514/264 |
| 5815919 | 1/1983 | Japan ................................... | 514/264 |

OTHER PUBLICATIONS

Belgian Patent Abstract 724,027 (11/68).
Chem. Abst. 89:80239k (1978).
Chem. Abst. 102:5944v (1984).
Chem. Abst. 98:166915a (1983).
Chemical Abstracts, 93:137888k (corresponding to FR 2,437,207).
Chemical Abstracts, 105:178225b (corresponding to DE 3,500,972).
Chemical Abstracts, 105:84956p (corresponding to BE 903,646).

*Primary Examiner*—Dale R. Ore
*Attorney, Agent, or Firm*—Ernest G. Szoke; Wayne C. Jaeschke; Henry E. Millson

[57] ABSTRACT

Sebosuppressive compositions comprising a cosmetically- and pharmaceutically-acceptable carrier and an antiseborrheic agent consisting essentially of a 4-alkoxy- or 4-(4-alkylbenzyloxy)-benzoic acid and a purine compound corresponding to the formula:

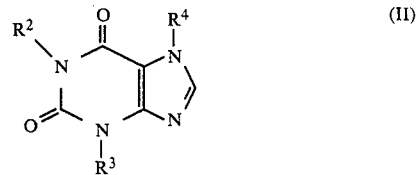

or the purine 1,3,7,9-tetramethyluric acid; or a physiologically-acceptable salt thereof. The antiseborrheic action of the 4-alkoxy- or 4-(4-alkylbenzyloxy)-benzoic acids is potentiated by the purine compounds. Preferred purine compounds are theophylline, theobromine and caffeine.

10 Claims, No Drawings

SEBOSUPPRESSIVE COMPOSITIONS AND METHOD FOR SUPPRESSING SEBACEOUS GLAND ACTIVITY

BACKGROUND OF THE INVENTION

1. Field of the Invention

The invention relates to topical sebosuppressive compositions for reducing sebaceous gland activity which include an antiseborrheic agent comprising a 4-alkoxy- or 4-(4-alkylbenzyloxy)-benzoic acid in combination with a purine compound.

Excessive secretion of the sebaceous glands of the scalp causes the hair to have a greasy appearance which is generally regarded as unaesthetic. Certain parts of the skin also tend toward excessive sebaceous gland activity which results in oily patches and causes a cosmetically unsatisfactory skin condition. Accordingly, modern cosmetology has directed efforts to normalize secretion of sebaceous glands by developing chemical treatments to restore the affected hair and skin to a healthy and attractive appearance.

2. Discussion of Related Art

Although several synthetic antiseborrheic products are known, many are not effective at safely non-toxic levels and there is a need for preparations which are effective at low dosages. It is particularly desirable to provide means for decreasing dosage levels of known, useful drugs while maintaining antiseborrheic efficacy.

4-alkoxybenzoic acids and physiologically acceptable salts thereof are known as antiseborrheic agents typically employed in cosmetic preparations, as described in German Patent Application P 35 00 972.1 According to the present invention, the antiseborrheic activity of these compounds is potentiated by certain purine compounds which do not themselves exhibit antiseborrheic activity in the amounts employed. The effective dosage of the 4-alkoxybenzoic acids is thus considerably reduced, while providing an antiseborrheic composition with no known adverse side effects.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The present invention comprises sebosuppressive compositions for topical application to the hair and the skin for reducing sebaceous gland activity. The compositions comprise a pharmaceutically acceptable carrier and an antiseborrheic agent which is a combination of:

(a) a 4-alkoxy- or 4-(4-alkylbenzyloxy)-benzoic acid corresponding to formula I:

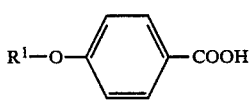

(I)

in which $R^1$ is $C_6$–$C_{18}$-alkyl, or 4-alkylbenzyl containing 4 to 12 carbon atoms in the alkyl moiety, or a physiologically acceptable salt thereof; and (b) a purine compound (I) which corresponds to the following formula II

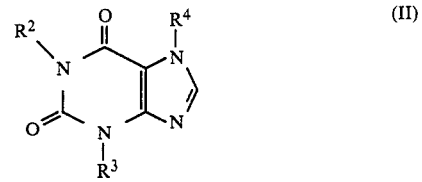

(II)

in which:

$R^2$ and $R^3$ independently of one another are hydrogen or methyl;

$R^4$ is hydrogen; methyl; —$CH_2$—$COOR^5$, wherein $R^5$ is hydrogen; or $C_1$–$C_4$-alkyl; or
—$CH_2$—$CH(OH)$—$CH_2$—$N(CH_3)CH_2$—$CH_2$—$OH$; or (ii) which is 1,3,7,9-tetramethyluric acid or (iii) a physiologically acceptable addition salt of (i) or (ii).

Preferably, the compound of formula I is a 4-alkoxybenzoic acid, in which $R^1$ is branched alkyl. Particularly suitable 4-alkoxybenzoic acids are, for example, 4-isooctyloxy, 4-isononyloxy, 4-isodecyloxy, 4-isotridecyloxy and 4-isooctadecyloxy benzoic acid.

4-(4-alkylbenzyloxy)-benzoic acids containing a branched alkyl, for example 4-(4-tert.-butylbenzyloxy)-benzoic acid, are also particularly suitable.

Suitable physiologically acceptable addition salts are, especially, alkali and alkaline-earth metal salts, for example sodium, potassium, calcium, or magnesium salts, and ammonium and alkanolammonium salts, for example, monoethanolammonium salt.

Some of the 4-alkoxy- or 4-(4-alkylbenzyloxy)-benzoic acids of formula I are known from the literature. In general, they are easily prepared by hydrolysis of the corresponding 4-alkoxy- or 4-(4-alkylbenzyloxy)-benzoic acid esters, for example the methyl or ethyl ester, under standard hydrolysis conditions. The 4-alkoxy- or 4-(4-alkyl-benzyloxy)-benzoic acid esters are in turn readily prepared by alkylation of p-hydroxybenzoic acid esters with alkylhalides, for example alkyl halides corresponding to the formula $R^1$—Cl; or alkyl sulfates, for example alkyl sulfates corresponding to the formula $R^1$—$OSO_3Na$; in which $R^1$ is as defined in formula I: all using standard methods.

Preferred purine compounds are theophylline, theobromine and caffeine. Theophylline-7-acetic acid and methyl and ethyl esters thereof; xantinol[7-(2-hydroxy-3-(2-hydroxyethyl)-methylaminopropyltheophylline]; xanthine; and 1,3,7,9-tetramethyluric acid are also especially effective. Suitable physiologically acceptable salts of the purine bases include the hydrochlorides, phosphates, carbonates, acetates, and citrates, as well as salts of other topically active acids, for example nicotinate which has circulation-promoting activity.

The active 4-alkoxy- or 4-(4-alkylbenzyloxy)-benzoic acids corresponding to formula I are preferably used in a quantity of from 0.001 to 0.5% by weight of the antiseborrheic compositions, while the purine compounds are used in an amount sufficient to potentiate the antiseborrheic activity of the benzoic acids, preferably in a quantity of from 0.01 to 5.0% by weight. The ratio by weight of 4-alkoxy- or 4-(4-alkylbenzyloxy)-benzoic acids to purine compounds in the compositions according to the invention is typically from 1:10 to 1:50. Frequently, the benzoic acids are used in an amount which exhibits little or no antiseborrheic activity, and are combined with the purines in an amount thereof sufficient to obtain the desired activity by potentiation of the antiseborrheic properties of the benzoic acids.

Suitable cosmetically- and pharmaceutically-acceptable carriers are those carriers known and used in preparatins intended for application to the hair or to the skin. Aqueous or alcoholic solutions, surfactant-containing lotions, and bases for oils, salves, emulsions, creams, gels and stick preparations are particularly suitable for the treatment of skin. Hair lotions, shampoos, medicated shampoos, hair rinses and hair sprays are particularly suitable for the treatment of hair. Because of the particular cosmetic problems caused by greasy hair, trichocosmetic preparations (i.e., hair treatment compositions having cosmetic utility) represent particularly preferred embodiments of the invention.

The antiseborrheic agent combination according to the invention of 4-alkoxy or 4-(4-alkylbenzyloxy)-benzoic acids and purines has a pronounced sebosuppessive action and exhibits good compatibility with the skin and mucous membranes. It also exhibits good compatibility with components typically present in cosmetic preparations, so that the agent is readily incorporated into a variety of cosmetics.

The most important components of standard cosmetic carriers are:

oil components: for example, paraffin oil, vegetable oil, fatty acid esters, squalene, fatty alcohols, 2-octyldodecanol;

fats and waxes: for example, spermaceti, beeswax, montan wax, paraffin, cetyl-stearyl alcohol;

emulsifiers: for example, fatty acid partial glycerides; fatty acid-sorbitan partial esters and their ethoxylates, soaps, fatty alcohol sulfates, fatty alcohol polyglycol ethers, alkyl phosphates;

washing-active substances: particularly anionic surfactants, for example, fatty alcohol polyglycol ether sulfates, fatty alcohol sulfates. α-olefin sulfonates, alkane sulfonates, sulfosuccinic acid esters, acyl taurides, acyl isethionates, and acyl sarcosines; ampholytic surfactants, for example, N-alkyl glycine, N-alkylaminopropionic acid, N-alkyl-aminobutyric acid containing from 8 to 18 carbon atoms in the alkyl group; zwitterionic surfactants, for example, N-alkyl-($C_8$–$C_{18}$)-N,N-dimethylammonioglycinate or N-cocosacylaminopropyl-N,N-dimethylammonioglycinate; and nonionic surfactants, for example fatty alcohol polyglycolethers, alkylphenol polyglycolethers, fatty acid polyglycolesters, amine oxide surfactants, fatty acid alkanolamides and their ethoxylates; and cationic surfactants, for example alkyl($C_{12}$–$C_{18}$)-trimethylammonium chloride, lauryldimethylbenzylammonium chloride, cetylpyridinium chloride, distearyldimethylammonium chloride:

lower alcohols: for example, ethanol, and isopropanol;

polyhydric alcohols: for example, ethyleneglycol, propyleneglycol, and glycerol;

water and auxiliaries: for example, perfumes, preservatives, buffers, thickeners, dyes and opacifiers.

The following Examples are intended to illustrate but not limit the invention.

EXAMPLES

I. Production of 4-alkoxybenzoic acids (A) 4-tetradecyloxybenzoic acid 20 g tetradecyloxybenzoic acid methyl ester were dissolved with 2.75 g sodium hydroxide in 80 ml ethanol and, after addition of 50 ml water, the resulting solution was heated for 2.5 hours to boiling temperature. After the suspension was concentrated by evaporation, the residue was dissolved in hot water and the resulting solution acidified with dilute acid. 18.2 g (95% of the theoretical) 4-tetradecyloxybenzoic acid melting at 95° to 99° C. (clear at 135° C.) were obtained after filtering, washing with water, and drying.

The following acids were obtained according to the process of Example IA from their corresponding methyl or ethylesters:

(B) 4-dodecyloxybenzoic acid
Melting point 94° to 95° C. (clear at 135° C.)

(C) 4-decyloxybenzoic acid
Melting point 97° to 98° C. ( clear at 120° C.)

(D) 4-isononyloxybenzoic acid (new compound)
Melting point 118° to 119° C.

(E) 4-(4-tert.-butylbenzyloxy)-benzoic acid (new compound)
Melting point 236° to 239° C.

(F) 4-isotridecyloxy benzoic acid (new compound)
Melting point 56° C. (beyond 36° C. sintering)

II Testing and evaluation of antiseborrheic activity

2.1 Basis

The test is based on the observation that male rats secrete a brownish sebum so that the more or less heavy greasiness of the skin may conveniently be visually assessed as browning of the skin. The fact that browning is caused by surface sebum is reflected in the fact that, after washing with surfactant solutions or with lipid solvents, young female rats and male rats only have the normal light, pink-colored skin after shaving. The same applies to male rats systematically treated with oestrogen. At the same time, only very small amounts of lipids can be extracted from the hair shaved off.

2.2 Procedure

The test animals were male Wistar rats having a body weight of 220 to 230 g at the beginning of the test.

In order to assess effectiveness, the test substances were each brushed onto half the back of 6 rats in the concentrations in ethanol/acetone (1:1) indicated in Table 1. The other half was only treated with the solvent.

Over the test period of 14 days, the test substances were applied once daily for a total of 9 days. A group of 6 rats which remained completely untreated was used as a control group. At the end of the test, the animals were shaved on their back and their sides and were visually accessed independently by an examination panel of 6 people under double blind conditions. The degree of browning on the back of the rats was visually assessed as a measure of the sebum coating.

2.3 Evaluation

The first criterion evaluated was the difference between the righthand side and the lefthand side, each examiner awarding 1 point per animal on the following basis:

| | | |
|---|---|---|
| darker side | 1 point | |
| lighter side | 0 point | |
| both sides the same | 0.5 point | |

Significant differences between the untreated and treated sides in this first method of evaluation indicate the local effectiveness of a substance.

The second criterion evaluated was the difference in intensity between the shades of brown using the following scale:

| | |
|---|---|
| 3 points | dark brown |
| 2 points | medium brown |
| 1 point | light brown |
| 0 point | no browning |

In this method of evaluation, the point total differences between the untreated control animals and the treated and untreated sides (ΔP) of the test animals are calculated, with significant differences between the control animals and the treated side of the test animals again indicating the effectiveness of a substance.

Percentage sebum reduction

The sebum reduction is calculated from the point total difference by calculating the quotient between the point difference ΔP and the number of points for the control group $P_k$ and expressing the value obtained in percent:

Sebum reduction = $(\Delta P/P_k) \times 100 (\%)$

TABLE 1

| Quantities in % by weight | | | | | | | | | | | |
|---|---|---|---|---|---|---|---|---|---|---|---|
| 4-dodecyloxybenzoic acid | 0.01 | — | — | — | — | — | — | — | — | 0.01 | — |
| 4-isononyloxybenzoic acid | — | 0.02 | — | — | — | — | 0.02 | — | — | — | — |
| 4-isotridecyloxybenzoic acid | — | — | 0.002 | 0.001 | — | — | — | 0.002 | 0.002 | — | 0.001 |
| Theophylline | — | — | — | — | 0.2 | — | 0.2 | 0.2 | 0.5 | — | — |
| Caffeine | — | — | — | — | — | 0.1 | — | — | — | 0.1 | 0.1 |
| Ethanol/acetone (1:1) | ad 100 | ad 100 | ad 100 | ad 100 | ad 100 | ad 100 | ad 100 | ad 100 | ad 100 | ad 100 | ad 100 |
| Percentage sebum reduction | 0 | 27 | 10 | 0 | 0 | 0 | 74 | 39 | 20 | 49 | 48 |

III. The following formulations exemplify antiseborrheic compositions according to the present invention.

| 3.1 | Shampoo for greasy hair | |
|---|---|---|
| | Texapon TM N 25 (1) | 40% by weight |
| | Comperian TM KD (2) | 3 |
| | 4-isononyloxybenzoic acid | 0.04 |
| | theophylline | 0.2 |
| | Bronidox TM L (3) | 0.2 |
| | water | ad 100 |
| 3.2 | Fast-acting hair treatment-emulsion | |
| | cetyl alcohol -11- | 3.0% by weight |
| | Dehyquart TM A (4) | 2.0 |
| | 4-isotridecyloxybenzoic acid | 0.02 |
| | theobromine | 0.2 |
| | citric acid | 1.0 |
| | water | ad 100 |
| 3.3 | Fast-acting hair treatment, clear | |
| | Cetiol TM HE (5) | 20.0% by weight |
| | cetyl pyridinium chloride | 5.0 |
| | glycerine | 5.0 |
| | 4-dodecyloxy benzoic acid | 0.05 |
| | caffeine | 0.1 |
| | isopropanol | ad 100 |
| 3.4 | Hair lotion | |
| | Cetiol TM HE (5) | 20.0% by weight |
| | birch extract | 1.0 |
| | 4-isononyloxybenzoic acid | 0.005 |
| | theophylline | 0.1 |
| | isopropanol | 30.0 |
| | water | ad 100 |
| 3.5 | Skin emulsion O/W | |
| | Cutina TM MD (6) | 7.0% by weight |
| | Eumulgin TM B1 (7) | 3.0 |
| | Cetiol TM SN (8) | 10.0 |
| | Myritol TM 318 (9) | 10.0 |
| | 4-isononyloxybenzoic acid | 0.01 |
| | theophylline | 0.01 |
| | Water | ad 100 |
| 3.6 | Skin cream O/W | |
| | Cutina TM MD (6) | 17% by weight |
| | Eumulgin TM B1 (7) | 3 |
| | Eutanol TM G (10) | 11 |
| | Myritol TM 318 (9) | 6 |
| | carrot oil CLR | 3 |
| | 4-isotridecyloxybenzoic acid | 0.01 |
| | theophylline | 0.1 |
| | water | ad 100 |

The trade names used in the Formulation Examples have the following meanings:

| | | |
|---|---|---|
| (1) | Texapon TM N 25: | 28% aqueous solution of alkyl-(C$_{12}$–C$_{14}$—poly(2EO)glycolether sulfate, Na-salt |
| (2) | Comperian TM KD: | coconut oil fatty acid diethanolamide |
| (3) | Bronidox TM L: | 5-bromo-5-nitro-1,3-dioxane (10% solution in 1,2-propyleneglycol) |
| (4) | Dehyquart TM A: | cetyltrimethyl ammonium chloride (25% solution in water) |
| (5) | Cetiol TM HE: | polyol fatty acid ester (CTFA name: PEG-7-glyceryl cocoate) |
| (6) | Cutina TM MD: | palmitic/stearic acid mono/diglyceride |
| (7) | Eumulgin TM B1: | cetyl/stearyl alcohol + 12 moles ethylene oxide |
| (8) | Cetiol TM SN: | cetyl/stearyl isononanoate |
| (9) | Myritol TM 318: | caprylic/capric acid triglyceride |
| (10) | Eutanol TM G: | 2-octyldodecanol |

We claim:

1. A sebosuppressive composition for suppressing activity of the sebaceous gland in mammals comprising a cosmetically and pharmaceutically-acceptable carrier and an antiseborrheic agent consisting essentially of:
   (a) from about 0.001 to about 0.5% by weight of (i) a 4-alkoxy- or 4-(4-alkylbenzyloxy)-benzoic acid having antiseborrheic activity corresponding to the formula I:

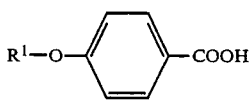

(I)

in which $R^1$ is $C_6$-$C_{18}$-alkyl or 4-alkylbenzyl containing from 4 to 12 carbon atoms in the alkyl group; or (ii) a physiologically acceptable salt thereof; and (b) from about 0.01 to about 5.0% by weight of a purine compound which:

(i) corresponds to the formula II:

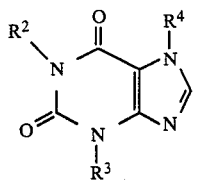

in which $R^2$ and $R^3$ independently of one another are hydrogen or methyl; and $R^4$ is hydrogen; methyl; —$CH_2$—$COOR^5$, in which $R^5$ is hydrogen or $C_1$-$C_4$-alkyl; or —$CH_2$—$CH(OH)$—$CH_2$—$N(CH_3)CH_2$—$CH_2$—$OH$; or (ii) is 1,3,7,9-tetramethyluric acid; or (iii) is a physiologically-acceptable salt of (i) or (ii).

2. The sebosuppressive composition of claim 1, wherein the compound of formula I is 4-isooctyloxy benzoic acid, 4-isononyloxy benzoic acid, 4-isodecyloxy benzoic acid, 4-isotridecyloxybenzoic acid, 4-isooctadecyloxybenzoic acid, 4-decyloxybenzoic acid or 4-dodecyloxybenzoic acid.

3. The sebosuppressive composition of claim 1, wherein the, purine is theophylline, theobromine, or caffeine.

4. The sebosuppressive composition of claim 2, wherein the purine is theophylline, theobromine, or caffeine.

5. The sebosuppressive composition of claim 1 wherein component (a) is 4-dodecyloxybenzoic acid, 4-isononyloxybenzoic acid, or 4-isotridecyloxybenzoic acid, and component (b) is theophylline or caffeine.

6. A method for suppressing sebaceous gland activity in mammals comprising topically applying the composition of claim 1 to the skin of said mammal in an amount sufficient to suppress the gland activity.

7. A method for suppressing sebaceous gland activity in mammals comprising topically applying the composition of claim 2 to the skin of said mammal in an amount sufficient to suppress the gland activity.

8. A method for suppressing sebaceous gland activity in mammals comprising topically applying the composition of claim 3 to the skin of said mammal in an amount sufficient to suppress the gland activity.

9. A method for suppressing sebaceous gland activity in mammals comprising topically applying the composition of claim 4 to the skin of said mammal in an amount sufficient to suppress the gland activity.

10. The method of claim 6, wherein the benzoic acid is present in the composition in an amount insufficient to substantially suppress sebaceous gland activity, and wherein the purine is present in a potentiating amount sufficient to impart gland-suppressing activity to the composition.

* * * * *